United States Patent [19]

Yamamoto

[11] Patent Number: 4,556,995
[45] Date of Patent: Dec. 10, 1985

[54] GOGGLES FOR SPORTS

[75] Inventor: Tamenobu Yamamoto, Osaka, Japan

[73] Assignee: Yamamoto Kagaku Co., Ltd., Osaka, Japan

[21] Appl. No.: 569,805

[22] Filed: Jan. 11, 1984

[30] Foreign Application Priority Data

Jan. 11, 1983 [JP] Japan ............................. 58-2460[U]
Jan. 11, 1983 [JP] Japan ............................. 58-2461[U]
Oct. 11, 1983 [JP] Japan ......................... 58-157794[U]

[51] Int. Cl.$^4$ ............................................. A61F 9/02
[52] U.S. Cl. ............................................ 2/439; 2/10; 2/427; 2/432; 2/437; 2/452
[58] Field of Search ................. 2/439, 427, 437, 426, 2/428, 430, 431, 452, 435, 9, 12, 206, 440, 436, 432, 434, 10

[56] References Cited

U.S. PATENT DOCUMENTS

| 2,388,205 | 10/1945 | Bernheim et al. | 2/437 X |
| 3,049,716 | 8/1962 | Stegeman | 2/12 X |
| 3,896,496 | 7/1975 | Leblanc et al. | 2/439 |
| 4,097,930 | 7/1978 | Bay | 2/10 |
| 4,264,988 | 5/1981 | Specht | 2/431 |
| 4,288,878 | 9/1981 | Helmbreck | 2/427 |
| 4,290,673 | 9/1981 | Yamamoto | 2/437 X |
| 4,309,775 | 1/1982 | Jory | 2/12 |
| 4,333,180 | 6/1982 | Bay | 2/10 |
| 4,447,914 | 5/1984 | Jannard | 2/432 |

Primary Examiner—Werner H. Schroeder
Assistant Examiner—J. L. K. Olds
Attorney, Agent, or Firm—Armstrong, Nikaido, Marmelstein & Kubovcik

[57] ABSTRACT

A frame for surrounding and holding the lens of goggles for sports comprises an upper frame member, opposite side frame members and a lower frame member which are formed integrally. A protector is provided along the front portion at least of the upper frame member of the frame.

8 Claims, 30 Drawing Figures

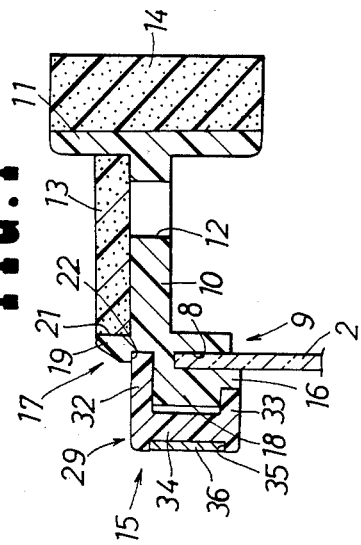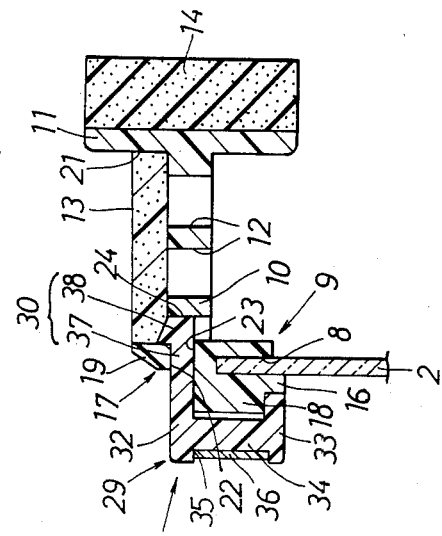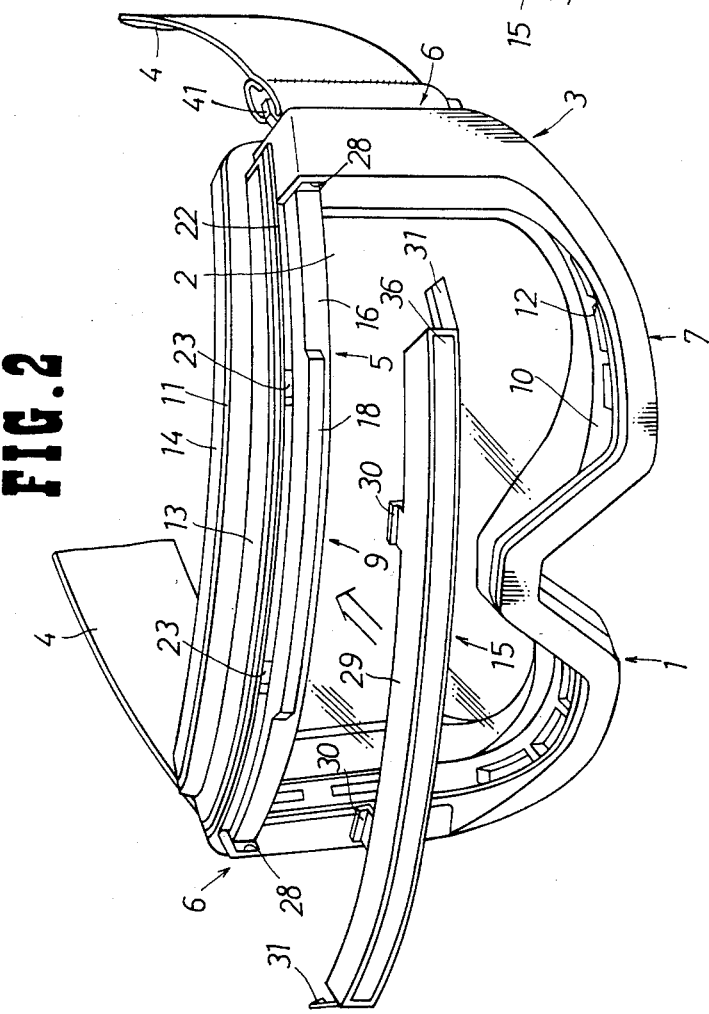

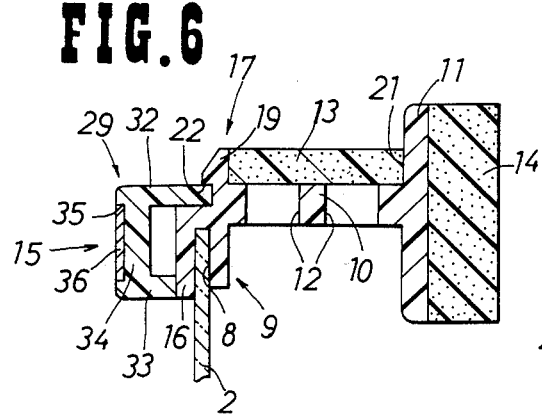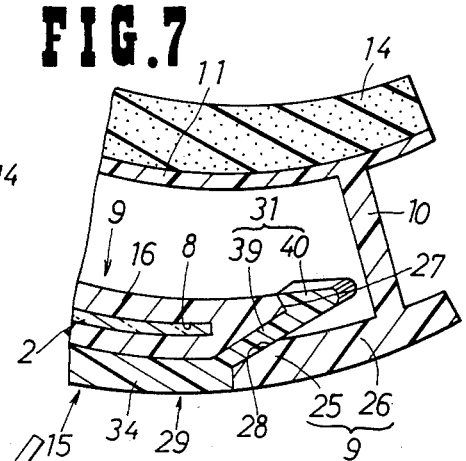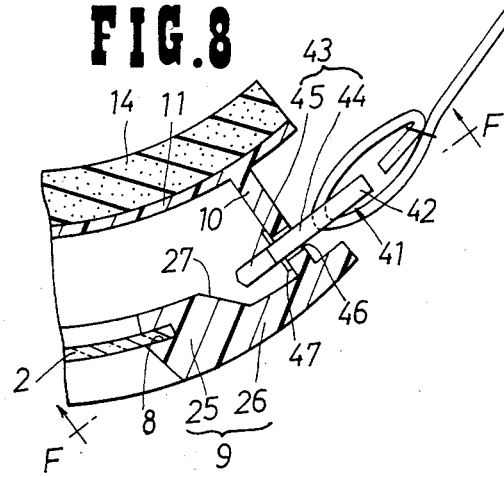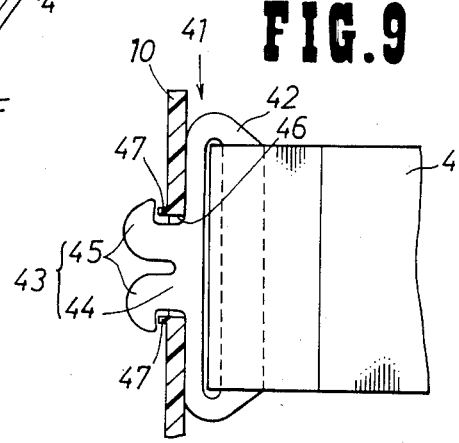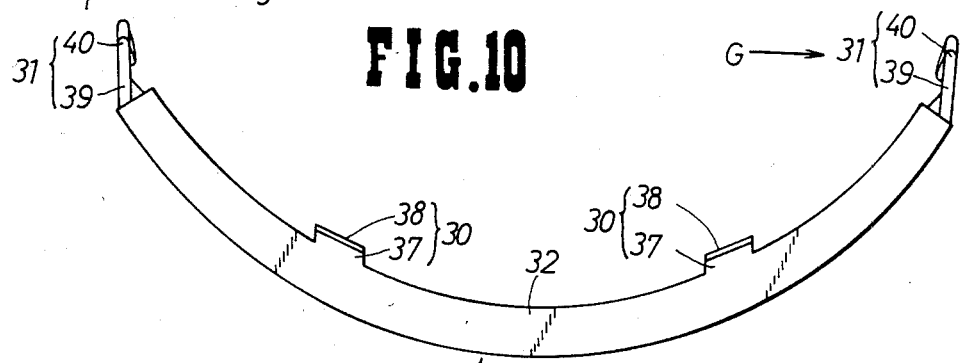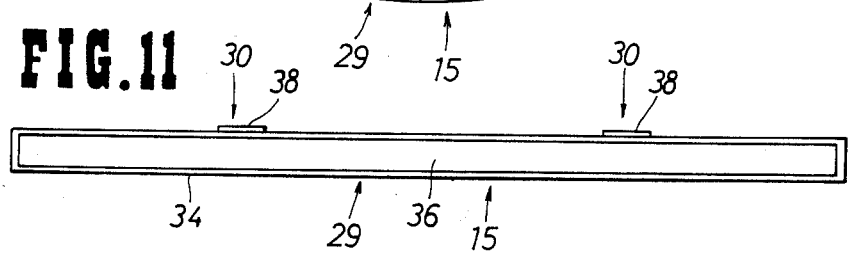

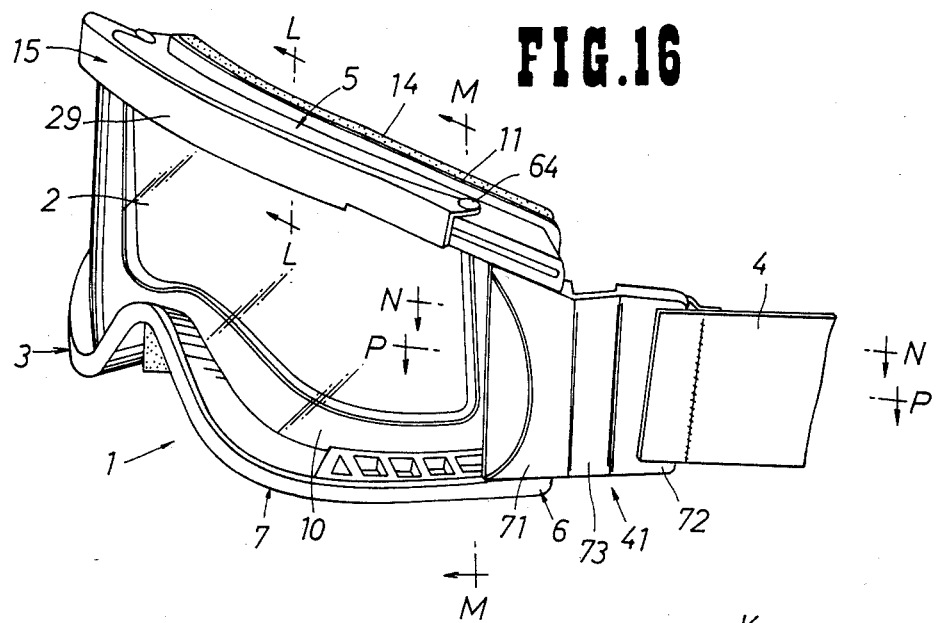
FIG.16
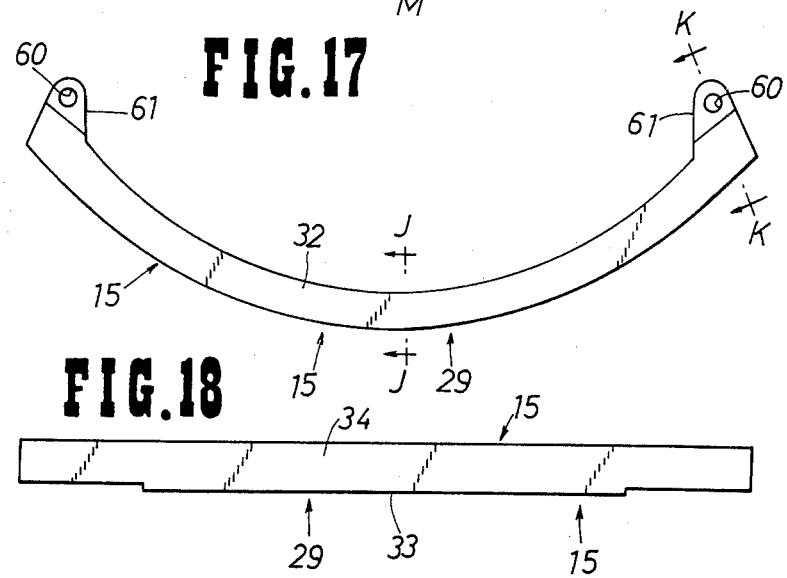
FIG.17
FIG.18
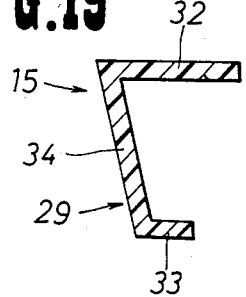
FIG.19

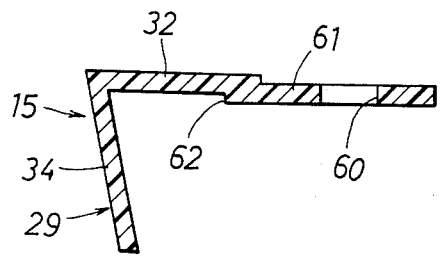
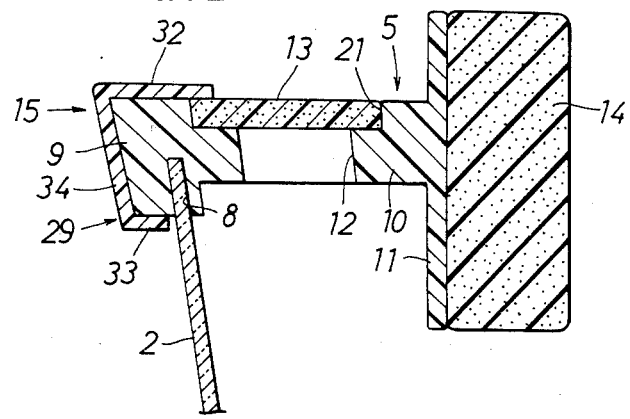
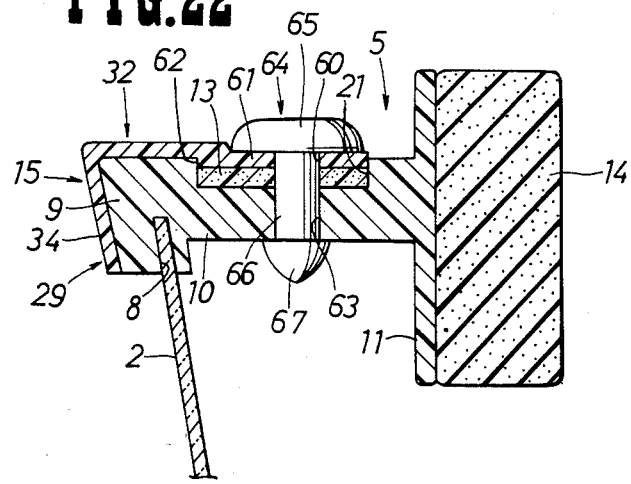

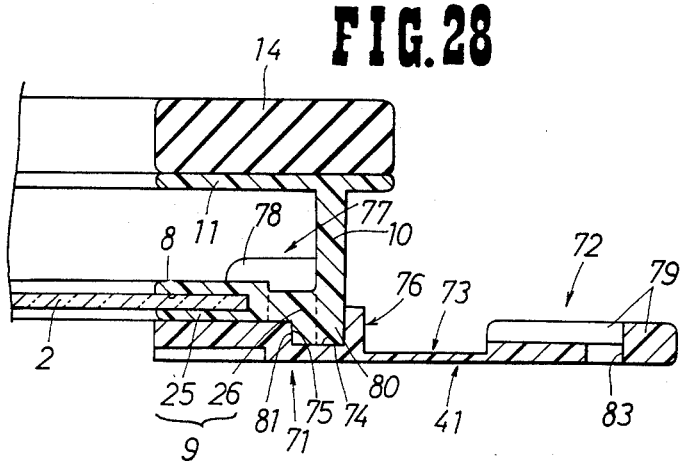
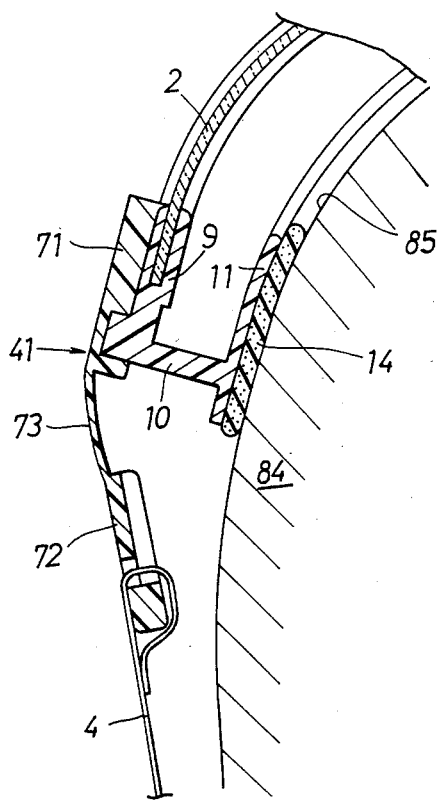
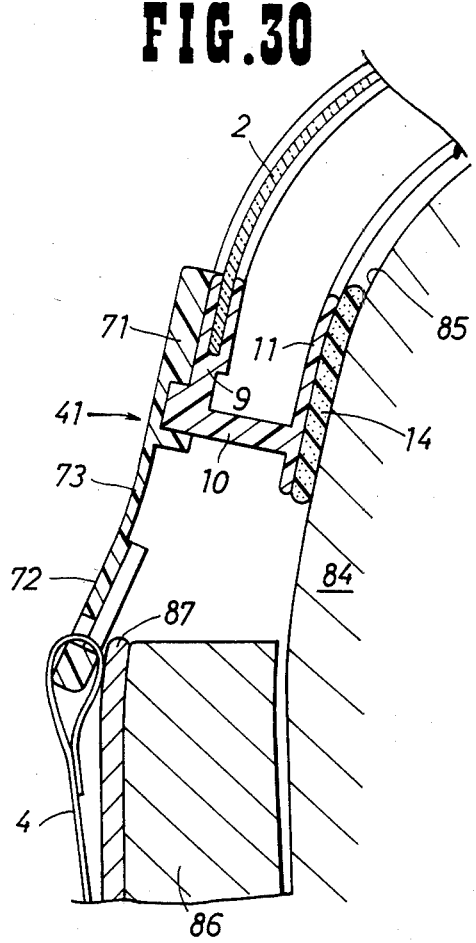

GOGGLES FOR SPORTS

BACKGROUND OF THE INVENTION

In ski races, such as slalom race and giant slalom race, the athlete skis zigzag between upright poles spaced apart on the ground to compete for time. To shorten the time, the athlete must glide on skis in a straight line to the greatest extent possible. This inevitably involves the likelihood that the athlete will collide with the pole. Since the athlete in this case glides in a forwardly inclined posture with his forehead positioned most forward, the forehead portion is most likely to collide with the pole. In recent years, the poles are supported upright by a spring and produce very great impact on collision.

On the other hand, the athlete wears goggles, which are usually provided with no protective means against collisions.

More specifically the goggles have a frame surrounding a lens for holding the lens and including an upper frame portion, opposite side frame portions and a lower frame portion which are made of a relatively soft synthetic resin as an integral piece. Conventionally, these portions are not provided with any protector or the like. For the reason given above, the upper frame portion of the frame is very likely to strike against the pole during races, but the conventional goggles are not provided with any means against a collision with the pole as stated above, so that the collision easily bends or deforms the frame, possibly permitting the resulting impact to act on the lens to break the lens.

Further the impact, if great, strongly acts on the forehead of the athlete to cause an injury. Even if the impact is small and does not break the lens, the goggles fitted to the face of the athlete will be improperly displaced by the deformation of the frame to entail the problem of causing trouble to the subsequent gliding.

SUMMARY OF THE INVENTION

A first object of the present invention is to provide goggles for sports which comprise a frame surrounding a lens for holding the same and a protector provided along the front portion at least of an upper frame member of the frame so that the protector withstands impact when the goggles collide with an obstacle to eliminate the likelihood of local deformation of the frame and prevent damage to the lens and displacement of the goggles from the proper worn position.

A second object of the present invention is to provide goggles for sports of the type described wherein the protector is elastic and adapted to absorb the impact of a collision as uniformly distributed over the entire body of the protector to assure safety by preventing the impact from acting on the body of the wearer with high intensity and to enable the skiing athlete to shorten the racing time by permitting him to strike against the pole rather positively during skiing.

A third object of the present invention is to provide goggles for sports of the type described wherein the protector is made easily attachable to the frame and has a main body of increased strength which is to be mounted on the upper frame portion.

A fourth object of the present invention is to provide goggles for sports which have a good appearance and in which the protector is effectively prevented from being displaced from the frame upward or downward and also from slipping off the frame forward by a simple structure.

A fifth object of the present invention is to provide goggles for sports of the type described above in which even when the protector should be broken by a collision with a pole or the like, the broken pieces are effectively prevented from scattering by a sticker which is adhered to the main body with a reduced likelihood of peeling off.

A sixth object of the present invention is to provide goggles for sports which are properly fittable to the face of the wearer irrespective of whether he wears a helmet.

Other objects, features and benefits of the present invention will become apparent from the following description with reference to the accompanying drawings.

BRIEF DESCRIPTION OF THE DRAWINGS

FIGS. 1 to 15 show a first embodiment of the present invention;

FIG. 1 is a perspective view of the goggles;

FIG. 2 is an exploded perspective view of the same;

FIG. 3 is a perspective view partly broken away and showing the goggles;

FIGS. 4 to 8 are views in section taken along the line A—A, line B—B, line C—C, line D—D and line E—E, respectively, of FIG. 1;

FIG. 9 is a view in section taken along the line F—F in FIG. 8;

FIG. 10 is a plan view of a protector;

FIG. 11 is a front view of the same;

FIG. 12 is a view showing the protector as it is seen in the direction of an arrow G in FIG. 10;

FIG. 13 is a rear view showing first and second connecting members attached to bands;

FIG. 14 is a rear view showing the bands partly and the first and second connecting members separated;

FIG. 15 is a view in section taken along the line H—H in FIG. 13;

FIGS. 16 to 30 show a second embodiment;

FIG. 16 is a perspective view of the goggles;

FIG. 17 is a plan view of a protector;

FIG. 18 is a front view of the same;

FIGS. 19 and 20 are views in section taken along the line J—J and the line K—K, respectively, of FIG. 17;

FIGS. 21 and 22 are views in section taken along the line L—L and the line M—M, respectively, of FIG. 16;

FIGS. 23 and 24 are sectional views showing exemplary fasteners;

FIG. 25 is a perspective view showing a connector;

FIG. 26 is a perspective view showing a side frame member;

FIGS. 27 and 28 are views in section taken along the line N—N and the line P—P, respectively, of FIG. 16; and FIGS. 29 and 30 are fragmentary plan views in section showing the functions of some parts.

DETAILED DESCRIPTION OF THE INVENTION

Figure 3:
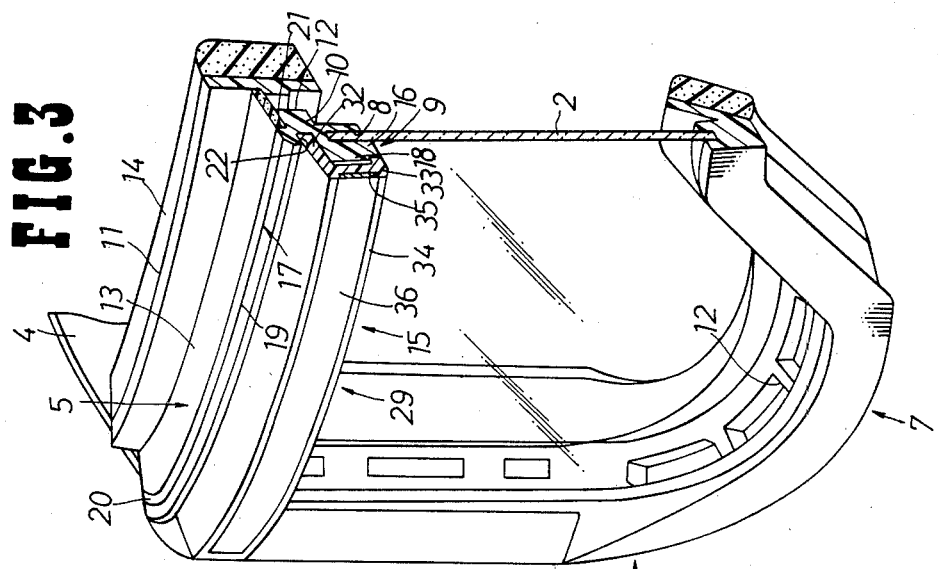
Figure 1:
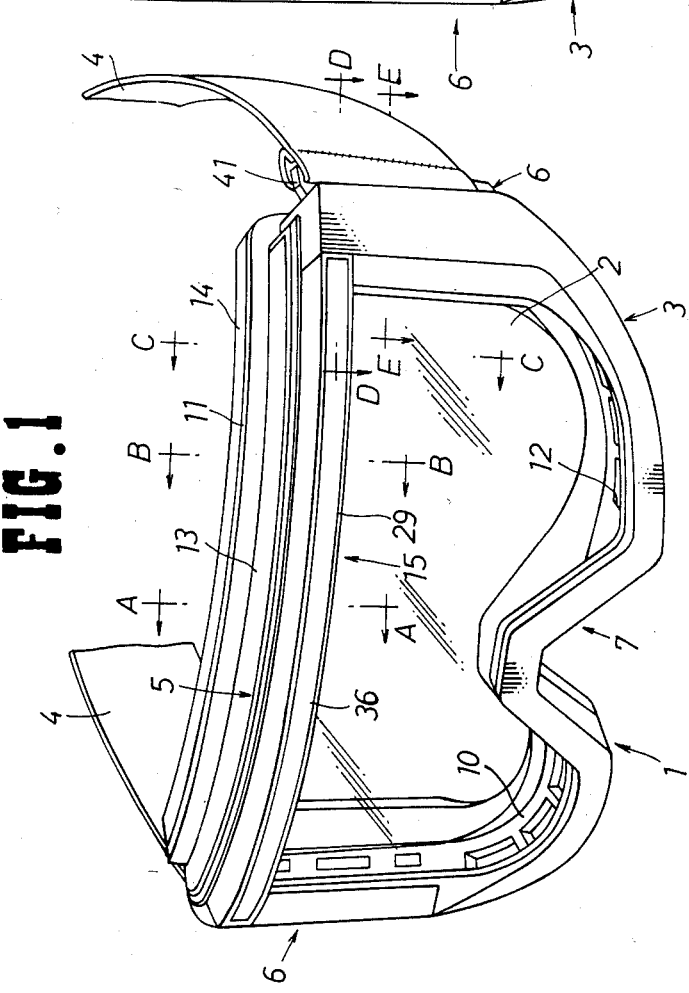
Figure 12:
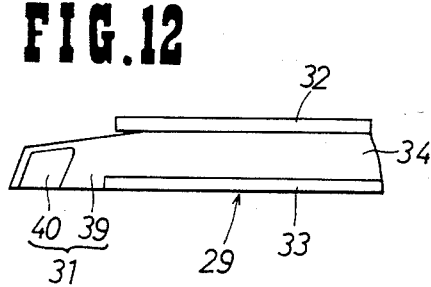
Figure 13:
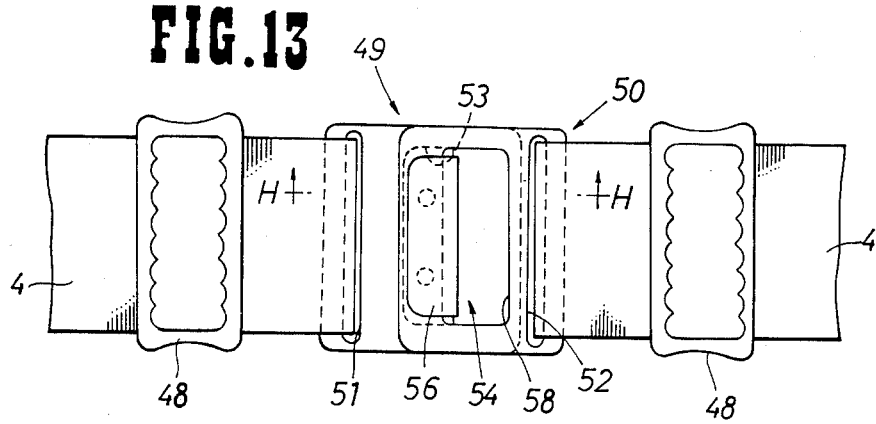
Figure 14:
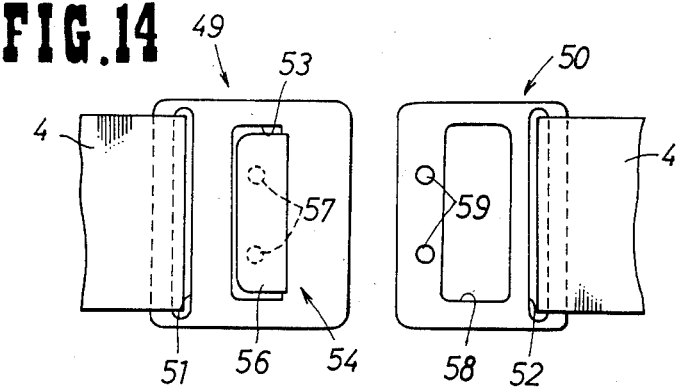
Figure 15:
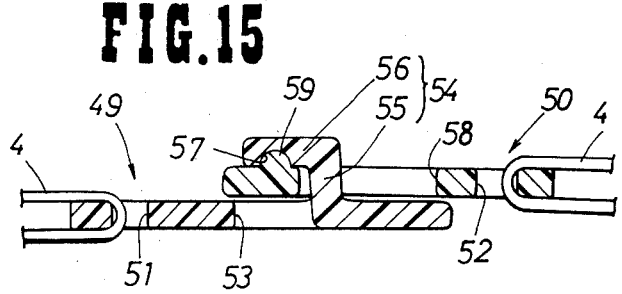

FIG. 1 to FIG. 15 show goggles 1 according to a first embodiment of the invention. As seen in FIGS. 1 to 3, the goggles 1 comprise a lens 2, a frame 3 surrounding and holding the lens 2 and a pair of opposite stretchable bands 4 for holding the goggles 1 to the head of the wearer.

The frame 3 is made of a flexible, deformable, relatively soft and elastic synthetic resin as an integral piece. The frame 3 comprises an upper frame member 5, opposite side frame members 6 and a lower frame member 7. At any portion of the entire periphery of the frame 3 including these members as seen in FIGS. 4 to 8, the frame is formed with a lens holder 9 having a groove 8 at its inner side, a strip wall 10 extending from its rear side and a flange 11 integral with the outer end of the wall 10 at right angles therewith. Suitable vents 12 in the form of openings of netting or the like are formed in the strip walls 10 of the upper frame member 5 and lower frame member 7 and in the upper portions of the strip walls 10 of the side frame members 6. A foam sheet 13 is adhered to the outer surfaces of the strip walls 10 for covering the vents 12. A foam pad 14 is adhered to the rear surfaces of the flanges 11.

A protector 15 is removably attached at least to the upper frame member 5 of the frame 3. For this purpose, the upper frame member 5 and the opposite side frame members 6 have the following construction.

With reference to FIGS. 4 to 6, the lens holder 9 of the upper frame member 5 comprises a lens mount 16 having the groove 8 for fitting the lens 2 therein, a connecting wall 17 projecting upward from the rear end of the lens mount 16 over the entire widthwise length thereof and interconnecting the lens mount 16 and the strip wall 10, and a forward projection 18 rectangular in cross section and projecting forward from the upper part of the middle portion of the lens mount 16.

The front surface of each side end of the lens mount 16 is positioned rearward from the front surface of the lens holder 9 of each side frame member 6, and the upper surface of the side end is positioned below the top surface of the lens holder 9.

The connecting wall 17 is joined, approximately at the midportion of its height, to the strip wall 10, and the upper portion of the connecting wall 17 projecting upward beyond the strip wall 10 is a surrounding wall portion 19 projecting forward beyond its lower portion. Each side end of the surrounding wall portion 19 is integral with a surrounding wall portion 20 projecting upward from the top surface of each side frame member 6 and generally L-shaped when viewed from above. The rear end of the surrounding wall portion 20 is integral with the flange 11. The space surrounded by the wall portions 19, 20 and the flange 11 is a recess 21 for accommodating the foam sheet 13 therein.

Between the surrounding wall portion 19 and the lens mount 16, the lower portion of the connecting wall 17 is formed with a rearwardly recessed fitting groove 22. The bottom wall of the fitting groove 22 is formed with a pair of opposite first insertion holes 23 in the form of a horizontally elongated rectangle.

Behind the connecting wall 17, the front side of the strip wall 10 of the upper frame member 5 is formed, in register with the first insertion holes 23 to the rear thereof, with a pair of opposite second insertion holes 24 shaped in corresponding relation to the first insertion holes 23.

Further as seen in FIGS. 7 and 8, the lens holder 9 of each side frame member 6 comprises a lens mount 25 positioned inward and a connecting wall 26 interconnecting the lens mount 25 and the strip wall 10. The lens holder 9 has a planar front surface. The lens mount 25 has a larger wall thickness than the connecting wall 26. The outward rear end of the lens mount 25, when seen from above, is slanted as at 27 with respect to the inner side of the mount 25 and to the rear surface of the connecting wall 26. The wall thickness of the lens mount 25 gradually decreases outward. A third insertion hole 28 extends through the upper end of the lens mount 25 from the inner side face of the mount 25 to the slanting face 27.

The protector 15 is integrally molded from a rigid synthetic resin or integrally press-formed from a thin metal plate and has a relatively high rigidity. As seen also in FIGS. 10 to 12, the protector 15 comprises a main body 29 extending over the entire widthwise length (approximately over the entire length) of the lens holder 9 of the upper frame member 5 on the front side thereof and having an enhanced function of protecting the upper frame member 5, a pair of opposite intermediate engaging pawls 30 projecting rearward from side portions of the main body 29 corresponding to the first insertion holes 23, and a pair of opposite side engaging pawls 31 projecting rearward from opposite side ends of the main body 29.

The main body 29 comprises horizontal upper and lower walls 32, 33, and a front wall 34 interconnecting the front ends of the upper and lower walls 32, 33 and is in the form of a channel which is open rearward. The main body 29 has great strength and is removably fitted to the forward projection 18 from the front, holding the projection from above and below, whereby the protector 15 is prevented from upward and downwward displacement from the upper frame member 5. The upper wall 32 is removably fitted at its rear end in the groove 22 and bears on the top of the lens mount 16 and the forward projection 18 of the upper frame member 5. The front wall 34 is opposed to the front surface of the forward projection 18 with a small clearance formed therebetween (or may be in contact therewith). The lower wall 33 is in contact with the bottom of the forward projection 18 and bears on the front face of the lower end of the lens mount 16. The lower surface of the lower wall 33 is flush with (or may be approximately flush with) the lower surface of the lens mount 16. Each side end of the main body 29 is in contact with the inner side surface of the lens mount 25 of each side frame member 6. The upper surface of each side end of the upper wall 32 is flush with (or may be approximately flush with) the top of the lens mount 25, and the front surface of each side end of the front wall 34 with the front surface of the lens mount 25. Since each surface of the main body 29 is flush (approximately flush) with the adjacent surface of the frame 3, the main body 29 and the frame 3 appear joined together and attractive. The main body has approximately over the entire length thereof except its opposite side ends a portion 35 recessed rearward and formed in the front side of the front wall 34. A sticker 36, with a strong adhesive backing, is adhered to the front surface of recessed portion 35 covering the recess from the bottom of the upper projection of element 29 to the top of the lower projection of element 29. Accordingly even if the protector 15 should be broken by a collision with a pole or the like, the broken pieces will be held together and effectively prevented from scattering by the sticker 36.

The protector 15 is prevented by the intermediate engaging pawls 30 from being displaced from the upper frame member 5 upward or downward and also from slipping off forward. The pawls project rearward from the rear end of the front wall 32. Each of the intermediate pawls 30 is composed of a horizontal base portion 37 having a uniform thickness and a tapered forward end engaging portion 38 having an upper portion projecting upward beyond the base portion 37. The pawls are removably insertable through the first and second insertion holes 23, 24 by virtue of elastic deformation of the upper frame member 5, and the base end face of each engaging portion 38 is engageable with the rear face of the connecting wall 17.

The side engaging pawls 31 primarily for preventing the protector 15 from slipping off the upper frame member 5 forward project rearward from side end portions of the front wall 34 and the lower wall 33 of the main body 29. The side engaging pawl 31, which is vertical, comprises a base portion 39 of uniform thickness and a tapered engaging portion 40 which has an inner portion projecting inward from the base portion 39. The pawl 31 is removably inserted into the side frame member 6 through the third insertion hole 38 by virtue of elastic deformation of the member, and the base end face of the engaging portion 40 is engaged by the slanting face 27. Since the engaging pawls 30, 31 are all positioned within the frame 3, the protector has a good appearance.

To attach the protector 15 to the frame 3, the side engaging pawl 31 at one side thereof is first inserted into and engaged with the side frame member 6. While thereafter fitting the upper wall 32 into the groove 22 to position the main body 29 over the forward projection 18, the intermediate engaging pawl 30 at the same side, the intermediate engaging pawl 30 at the other side and the side engaging pawl 31 at the other side are inserted into and engaged with the upper frame member 5 or the other side frame member 6 in the order mentioned, whereby the protector 15 can be installed in place easily.

The protector 15 is easily removable from the frame 3 by a procedure opposite to the above.

Since the protector 15 is provided for the upper frame member 5 which is very likely to collide with a pole or like obstacle, the protector 15 withstands impact in the event of a collision with the obstacle to render the frame 3 free of local deformation and prevent damage to the lens 2. The goggles are further prevented from displacement from the proper worn position. Furthermore great impact is first borne by the protector 15 and then absorbed by the elastic frame 3 as distributed over the entire body of the protector 15 without acting on the body of the wearer with great intensity, hence safety is assured. In other words, this enables the athlete to shorten the race time by permitting him to glide with a positive likelihood of striking against poles. The goggles are useful in contributing to safety not only for ski or time races but also for sports in general.

With reference to FIGS. 8 and 9, the base portion of each band 4 is removably attached to the strip wall 10 of each side frame member 6 by a connector 41. The connector 41, which is molded integrally from a rigid synthetic resin, comprises a trapezoidal frame portion 42, and a bifurcated attaching member 43 projecting forward from the vertical midportion of front side of the frame portion 42. The base portion of the band 4 is fastened to the frame portion 42 by a known method. The attaching member 43 comprises a bifurcated base portion 44 and a pair of upper and lower tapered engaging portions 45 extending from the upper and lower forward ends of the base portion 44. The upper engaging portion 45 extends from the base portion 44 upward, while the lower engaging portion 45 extends from the base portion 44 downward. The attaching member 43 is removably inserted in the side frame 6 through a vertically elongated attaching slit 46 formed in the side strip wall 10 of the side frame member 6, by virtue of elastic deformation of the strip wall 10, with the base end faces of the engaging portions 45 in engagement with the inner side surface of the strip wall 10. The upper and lower edges of the strip wall 10 defining the attaching slit 46 project inward to provide a pair of upper and lower protrusions 47.

Each band 4 has an adjusting member 48 for adjusting the length thereof. To detachably connect the two bands 4 together, a first connecting member 49 is attached to one of the free ends of the bands 4, and a second connecting member 50 to the other free end.

The connecting members 49, 50 are each in the form of a rectangular frame integrally molded from a rigid resin and are formed, each at the base portion, with vertical connecting slits 51, 52, respectively, for connecting the free ends of the bands 4.

The first connecting member 49 is formed with an opening 53 positioned toward its forward end. An L-shaped projection 54 extending rearward from the forward inner edge of the member 49 defining the opening 53 approximately over the entire length of the edge. The projection 54 comprises a base portion 55 at right angles to the main body of the first connecting member 54, and a free end portion 56 positioned in the rear of and opposed to the opening 53. A pair of upper and lower semispherical engaging dents 57 are formed in the front surface of the free end portion 56.

The second connecting member 50, which is to be positioned over the rear side of the main body of the first connecting member 49 other than the projection 54, is formed with an aperture 58 in the form of a vertically elongated rectangle and positioned toward its free end for the projection 54 to be inserted therethrough removably. The forward end of the second connecting member 50 is removably insertable into the space between the main body of the first connecting member 49 and the free end portion 56 of the projection 54 and is formed on the rear side with a pair of upper and lower, rearwardly projecting, semispherical engaging protrusions 59 which are engageable in the dents 57 by virtue of elastic deformation.

Accordingly the two connecting members 49 and 50 can be joined together by inserting the projection 54 of the first connecting member 49 into the aperture 58 of the second connecting member 50, inserting the forward end of the second connecting member 50 into the space between the main body of the first connecting member 49 and the free end portion 56 of the projection 54 and engaging the protrusions 59 in the dents 57.

The two connecting members 49 and 50 can be separated by a procedure reverse to the above.

FIGS. 16 to 30 show a second embodiment of the invention. With reference to FIGS. 16 to 20, a protector 15 has a front wall 34 and a lower wall 33 extending rearward from the middle portion of the front wall 34. A bracket 61 formed with an insertion hole 60 extends rearward from each end of the upper wall 32 of the protector 15. A stepped portion 62 is formed on the bottom side of the upper wall 32 and the bracket 61.

With reference to FIGS. 21 and 22, vents 12 formed in the strip wall 10 of an upper frame member 5 are covered with a foam sheet 13 which is accommodated in a recess 21 formed in the strip wall 10. The strip wall 10 has an insertion hole 63 positioned toward each side end thereof adjacent to the vent 12 and corresponding to the hole 60 of the bracket 61.

The main body 29 of the protector 15 is fitted over the lens holder 9 of the upper frame member 5, with the upper wall 32 bearing on the upper surface of the lens holder 9 and the front wall 34 in contact with the front surface of the lens holder 9. Each bracket 61 compresses from above the side end portion of the foam sheet 13 in the recess, and the stepped portion is in engagement with the front inner face defining the recess 21 at the side end portion.

Each of a pair of fasteners 64 is inserted through the hole 61 of the bracket 61 and the hole 63 of the strip wall 10 for fastening the bracket 61 to the strip wall 10. The fastener 64 comprises a head 65, a shank 66 extending downward from the head 65 and a leg 67 formed at the lower end of the shank 66 and bulging in the form of an inverted umbrella. The leg 67 is inserted through the hole 60 in the bracket 61, then passed through the foam sheet 13 and forced through the hole 63 of the strip wall 10, whereby the fastener is fitted in place.

Figure 23:
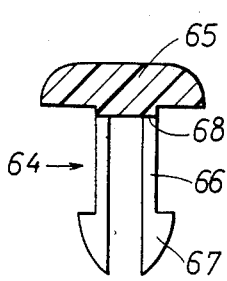

When the fastener 64 is made of a flexible synthetic resin, with a cutout 68 formed in the leg 67 and the shank 66 as seen in FIG. 23, the fastener 64 can be removably fitted in place with ease.

Figure 24:
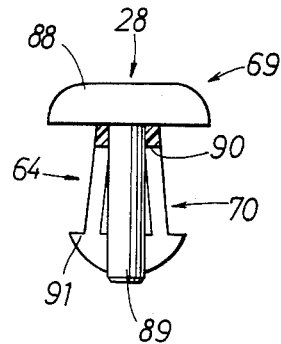
Figure 26:
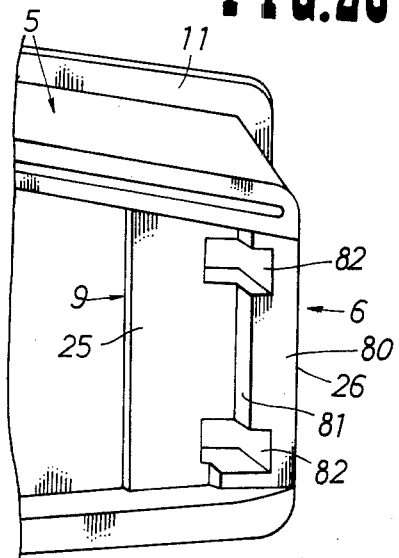
Figure 25:
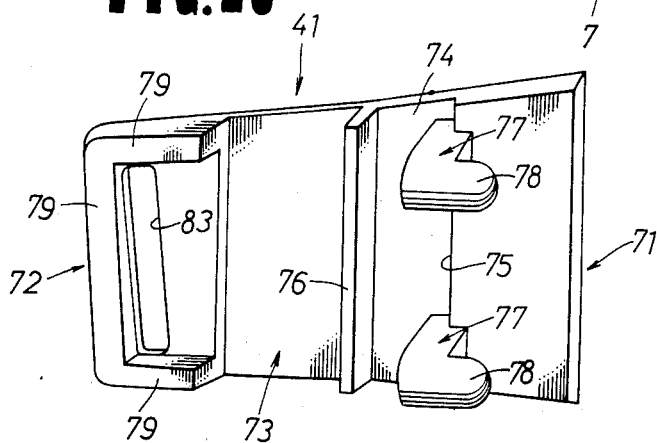

FIG. 24 shows another fastener 64 comprising a male member 69 and a female member 70 in combination. The male member 69 has a head 88 and a shank 89 extending downward therefrom. The female member 70 has legs 91 which are diametrically divided by a cut groove 90. When the shank 89 of the male member 69 is inserted into the female member 70, the legs 91 are forced outward away from each other.

Each of a pair of connectors 41 is attached to each end of a single band 4. The connector 41 comprises an attaching portion 71 attached in a fixed position to the side frame member 6, an undeformable rigid interconnecting portion 72 and a flexible portion 73 provided between the attaching portion 71 and the interconnecting portion 72. These portions 71 to 73 are in the form of an integral piece.

With reference to FIGS. 25 to 28, the attaching portion 71 of the connector 41 has a large thickness and is formed with a vertical groove 74 on its inner side (rear side). The groove 74 is defined by a stepped portion 75 of the thick part of the portion 71 and a rear rib 76. A pair of upper and lower projections 77 is formed at the stepped portion and in the vicinity thereof. The free end of each projection 77 is bent in a direction opposite to the rib 76 to serve as an approximately L-shaped engaging portion 78.

The flexible portion 73 of the connector 41 has a small thickness, is flexible and serves as a spring which elastically restores its substantially planar form at all times.

The interconnecting portion 72 of the connector 41 has an increased thickness in its entirety, is formed with a vertical slit to provide a band insertion holding portion 83 and has reinforcing ribs 79 along its three sides.

The connector 41 is integrally molded from a synthetic resin.

The connecting wall 17 of the side frame member 6 is integrally formed on its outer side with a vertical projection 80, whereby a stepped portion 81 is formed on the outer side of the connecting wall 17. A pair of upper and lower engaging holes 82 are formed in the stepped portion 81 and in the vicinity thereof.

Figure 27:
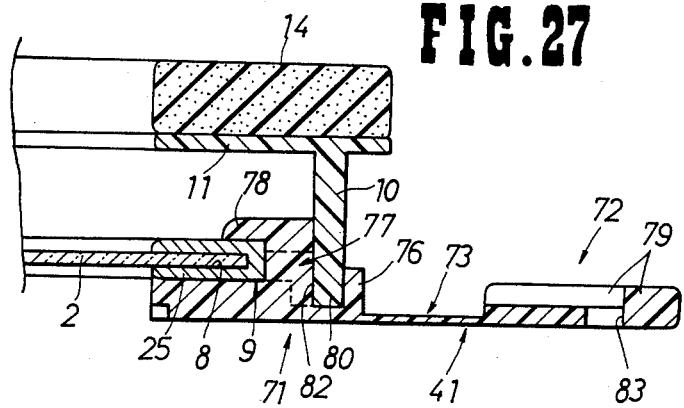

As seen in FIGS. 27 and 28, the projections 77 are fitted in the holes 82, whereby the attaching portion 71 of the connector 41 is fixedly attached to the side frame member 6. In this state, the engaging portions 78 of the projections 77 are fittingly engaged with the inner side face of the lens mount 16, the projection 80 is engaged in the groove 74, the stepped portions 75 and 81 are in engagement with each other, and the rib 76 is in contact with the rear surface of the connecting wall 17, whereby the attaching portion 71 is joined to the side frame member 6. The attaching portion 71 is removable from the side frame member 6 by forcibly drawing the projections 77 out from the engaging holes 82.

The interconnecting portions 72 of the connectors 41 are fastened to opposite ends of the band 4 by a known method, with the band passed through the holding portions 83. The term "opposite ends of the band 4" is not always limited to those of the band 4 in accurate sense.

The function of the band connector will be described. When the goggles 1 are worn by the wearer directly on the head 84 as seen in FIG. 29, the flexible portion 73 of the connector 41 bends like a hinge to suitably fit the band around the head 84, with a foam pad 14 on the frame 3 in intimate contact with the face 85 as in the prior art.

When the goggles 1 are worn with a helmet 86 on the head as seen in FIG. 30, the interconnecting portion 72 of the connector 41 is positioned on an opening edge 87 of the helmet 86. By the band 4, the portion 72 is held in an inclined position on the opening edge 87. Thus, despite the displacement of the interconnecting portion 72, the attaching portion 71 is held in place by the flexibility of the flexible portion 73, consequently holding the foam pad 14 on the frame 3 in intimate contact with the face 85. Moreover, the flexible portion 73 in the bent state functions as a spring acting to elastically restore itself, biasing the attaching portion 71 in the direction of arrow shown to thereby hold the side frame member 6 in intimate contact with the face 85 with improved effectiveness.

Although the protector 15 is provided on the upper frame member 5 of the frame 3 according to the foregoing embodiments, the protector 3 may be provided on the lower frame member 7 and/or the side frame members 6 of the frame 3.

What is claimed is:

1. Goggles for sports comprising a lens, a soft deformable frame surrounding the lens for holding the lens and including an upper frame member, opposite side frame members and a lower frame member, and a protector which is hard, almost undeformable and separate from the frame provided along the front portion of at least the upper frame member of the frame.

2. Goggles as defined in claim 1 wherein the upper frame member is made of an elastic material, and the protector is removably provided on the upper frame member and comprises a main body extending along the upper frame member front portion approximately over the entire length thereof, at least the middle portion of the main body being in the form of a channel which is open rearward, the main body being fitted to the upper frame member portion of the deformable frame from the front and holding the front portion from above and below, a pair of opposite intermediate engaging pawls projecting rearward from side portions of the main body, and a pair of opposite side engaging pawls projecting rearward from opposite side ends of the main body.

3. Goggles as defined in claim 2 wherein the main body is provided at its side ends with a pair of opposite engaging pawls inserted and engaged in the side frame members.

4. Goggles as defined in claim 2 wherein the main body is provided at a longitudinally intermediate portion thereof with an intermediate engaging pawl projecting rearward and inserted and engaged in the upper frame member.

5. Goggles as defined in claim 2 wherein the main body is provided at each side end thereof with a fastener for attaching the side end to the frame.

6. Goggles as defined in claim 2 wherein the upper surface of each side end portion of the main body is approximately flush with the top surface of each of the side frame members, and the front surface of each side end portion of the main body is approximately flush with the front surface of each of the side frame members.

7. Goggles for sports having a soft deformable frame surrounding a lens for holding the lens and including an upper frame member, opposite side frame members and a lower frame member, the goggles being characterized in that a protector which is hard, almost undeformable and separate from the frame is provided along the front portion at least of the upper frame member of the frame approximately over the entire length of the upper frame member front portion, a recessed portion being formed in the protector approximately over the entire length thereof, a sticker being adhered to the inner surface of the recessed portion approximately over the entire length thereof.

8. Goggles for sports having a frame surrounding a lens for holding the lens and including opposite side frame members, each of the side frame members being provided with a connector for connecting a band thereto, the goggles being characterized in that the connector comprises an attaching portion engageable in a fixed position to the side frame member and overlapping the outside of said side frame member, extensions attached to said attaching portion and engageable with an inner margin of said side frame member, and a planar flexible portion integrally molded to said attaching portion and said extensions and projecting rearward as an extension of said attaching portion, said planar flexible portion terminating in a rib projecting perpendicular to said planar flexible portion and engagable with the rearmost portion of said side frame member, an undeformable rigid interconnecting portion retaining the band inserted therethrough having reinforcing ribs of a thickness sufficient to effectively resist deformation by said band, and a flexible intermediate portion connecting the attaching portion to the interconnecting portion having a generally rectangular or trapezoidal profile and a thickness less than that of the portions to which it is attached, the flexible intermediate portion being deformable to a curved form to fit the interconnecting portion and the band around the head or a helmet, but almost undeformable except in the curved form.

* * * * *